(12) United States Patent
Barrett et al.

(10) Patent No.: US 8,894,607 B2
(45) Date of Patent: Nov. 25, 2014

(54) TIP CONFIGURATIONS FOR MULTI-LUMEN CATHETER (71) Applicant: C. R. Bard, Inc., Murray Hill, NJ (US)

(72) Inventors: Joseph Barrett, Kaysville, UT (US); Dallen G. Herzog, Salt Lake City, UT (US); Amir Orome, Sandy, UT (US)

(73) Assignee: C. R. Bard, Inc., Murray Hill, NJ (US)

( * ) Notice: Subject to any disclaimer, the term of this patent is extended or adjusted under 35 U.S.C. 154(b) by 0 days.

(21) Appl. No.: 13/687,919

(22) Filed: Nov. 28, 2012

(65) Prior Publication Data

US 2013/0085436 A1    Apr. 4, 2013

Related U.S. Application Data

(62) Division of application No. 10/884,291, filed on Jul. 2, 2004, now Pat. No. 8,323,227.

(51) Int. Cl.
*A61M 25/00* (2006.01)
*A61M 1/36* (2006.01)
*A61M 39/02* (2006.01)
*A61M 39/10* (2006.01)
*A61M 1/16* (2006.01)

(52) U.S. Cl.
CPC ............ *A61M 39/02* (2013.01); *A61M 25/007* (2013.01); *A61M 25/0026* (2013.01); *A61M 25/0032* (2013.01); *A61M 2025/0031* (2013.01); *A61M 1/3661* (2014.02); *A61M 25/0068* (2013.01); *A61M 2025/0036* (2013.01); *A61M 1/3653* (2013.01); *A61M 39/105* (2013.01); *A61M 1/16* (2013.01); *A61M 2025/0073* (2013.01); *A61M 25/003* (2013.01)
USPC .......................................................... 604/43

(58) Field of Classification Search
CPC ............ A61M 2025/0031; A61M 2025/0037; A61M 25/0029; A61M 25/0068; A61M 25/007; A61M 25/0028; A61M 25/0032; A61M 2001/3661; A61M 2025/0034; A61M 1/16; A61M 25/003; A61M 25/008
USPC ............................. 604/39, 43, 523, 6.09, 6.16
See application file for complete search history.

(56) References Cited

U.S. PATENT DOCUMENTS 1,696,018 A    12/1928    Scheliberg
2,393,002 A    1/1946    Smith
(Continued)

FOREIGN PATENT DOCUMENTS

EP    0495263 A1    7/1992
EP    0711574 A1    5/1996
(Continued)

OTHER PUBLICATIONS

PCT/US2005/023451 filed Jun. 30, 2005 International Preliminary Report on Patentability dated Jan. 9, 2007.
(Continued)

*Primary Examiner* — Aarti B Berdichevsky
(74) *Attorney, Agent, or Firm* — Rutan & Tucker, LLP (57) ABSTRACT

Multi-lumen catheters with improved tip configurations, including a triple-lumen catheter which may be useful for apheresis. In one variation, the catheter has three lumens with distal openings angularly spaced apart and staggered axially with respect to one another. In another variation, the catheter has two lumens exiting distally and one centrally positioned lumen exiting proximally. A third variation is a catheter with a single distal opening and two proximal openings. The staggered lumen openings along the axial length of the catheter may decrease recirculation while maximizing flow rates.

10 Claims, 7 Drawing Sheets

(56) References Cited

U.S. PATENT DOCUMENTS

| | | |
|---|---|---|
| 3,256,885 A | 6/1966 | Higgins et al. |
| 3,416,532 A | 12/1968 | Grossman |
| 3,426,759 A | 2/1969 | Smith |
| 3,812,851 A | 5/1974 | Rodriguez |
| 3,929,126 A | 12/1975 | Corsaut |
| 3,995,623 A | 12/1976 | Blake et al. |
| 4,072,146 A | 2/1978 | Howes |
| 4,129,129 A | 12/1978 | Amrine |
| 4,149,535 A | 4/1979 | Volder et al. |
| 4,180,068 A | 12/1979 | Jacobsen et al. |
| 4,385,631 A | 5/1983 | Uthmann et al. |
| 4,406,656 A | 9/1983 | Hattler et al. |
| 4,451,252 A | 5/1984 | Martin et al. |
| 4,468,216 A | 8/1984 | Muto |
| 4,493,696 A | 1/1985 | Uldall et al. |
| 4,557,261 A | 12/1985 | Rugheimer et al. |
| 4,563,180 A | 1/1986 | Jervis et al. |
| 4,583,986 A | 4/1986 | Lapidus |
| 4,626,240 A | 12/1986 | Edelman et al. |
| 4,643,711 A | 2/1987 | Bates |
| 4,666,426 A | 5/1987 | Aigner et al. |
| 4,668,221 A | 5/1987 | Luther |
| 4,681,564 A | 7/1987 | Landreneau |
| 4,681,570 A | 7/1987 | Dalton |
| 4,682,978 A | 7/1987 | Martin et al. |
| 4,687,471 A | 8/1987 | Twardowski et al. |
| 4,755,176 A | 7/1988 | Patel |
| 4,772,269 A | 9/1988 | Twardowski et al. |
| 4,808,155 A | 2/1989 | Mahurkar |
| 4,842,582 A | 6/1989 | Mahurkar |
| 4,863,441 A | 9/1989 | Lindsay et al. |
| 4,867,742 A | 9/1989 | Calderon |
| 4,894,057 A | 1/1990 | Howes |
| 4,895,561 A | 1/1990 | Mahurkar |
| 4,935,044 A | 6/1990 | Schoenpflug et al. |
| 4,961,809 A | 10/1990 | Martin et al. |
| 4,981,477 A | 1/1991 | Schon et al. |
| 4,985,014 A | 1/1991 | Orejola |
| 4,995,865 A | 2/1991 | Gahara et al. |
| 5,015,230 A | 5/1991 | Martin et al. |
| 5,041,107 A | 8/1991 | Heil, Jr. |
| 5,053,004 A | 10/1991 | Markel et al. |
| 5,053,023 A | 10/1991 | Martin |
| 5,057,073 A | 10/1991 | Martin |
| 5,106,376 A | 4/1992 | Mononen et al. |
| 5,135,599 A | 8/1992 | Martin et al. |
| 5,156,592 A | 10/1992 | Martin et al. |
| 5,167,623 A | 12/1992 | Cianci et al. |
| 5,171,216 A | 12/1992 | Dasse et al. |
| 5,171,227 A | 12/1992 | Twardowski et al. |
| 5,188,593 A | 2/1993 | Martin |
| 5,190,520 A | 3/1993 | Fenton, Jr. et al. |
| 5,195,962 A | 3/1993 | Martin et al. |
| 5,209,723 A | 5/1993 | Twardowski et al. |
| 5,215,527 A | 6/1993 | Beck et al. |
| 5,221,255 A | 6/1993 | Mahurkar et al. |
| 5,221,256 A | 6/1993 | Mahurkar |
| 5,226,880 A | 7/1993 | Martin et al. |
| 5,242,398 A | 9/1993 | Knoll et al. |
| 5,324,274 A | 6/1994 | Martin |
| 5,342,295 A | 8/1994 | Imran |
| 5,346,471 A | 9/1994 | Raulerson |
| 5,348,536 A | 9/1994 | Young et al. |
| 5,350,358 A | 9/1994 | Martin |
| 5,374,245 A | 12/1994 | Mahurkar |
| 5,378,230 A | 1/1995 | Mahurkar |
| 5,395,316 A | 3/1995 | Martin et al. |
| 5,399,168 A | 3/1995 | Wadsworth, Jr. et al. |
| 5,403,274 A | 4/1995 | Cannon |
| 5,405,320 A | 4/1995 | Twardowski et al. |
| 5,405,341 A | 4/1995 | Martin |
| 5,451,206 A | 9/1995 | Young |
| 5,451,233 A | 9/1995 | Yock |
| 5,472,417 A | 12/1995 | Martin et al. |
| 5,472,432 A | 12/1995 | Martin |
| 5,486,159 A | 1/1996 | Mahurkar |
| 5,505,710 A | 4/1996 | Dorsey, III |
| 5,509,897 A | 4/1996 | Twardowski et al. |
| 5,569,182 A | 10/1996 | Twardowski et al. |
| 5,571,093 A | 11/1996 | Cruz et al. |
| 5,607,462 A | 3/1997 | Imran |
| 5,616,137 A | 4/1997 | Lindsay |
| 5,624,392 A | 4/1997 | Saab |
| 5,643,226 A | 7/1997 | Cosgrove et al. |
| 5,665,067 A | 9/1997 | Linder et al. |
| 5,685,865 A | 11/1997 | Cosgrove et al. |
| 5,685,867 A | 11/1997 | Twardowski et al. |
| 5,693,030 A | 12/1997 | Lee et al. |
| 5,718,678 A | 2/1998 | Fleming, III |
| 5,718,692 A | 2/1998 | Schon et al. |
| 5,738,649 A | 4/1998 | Macoviak |
| 5,743,891 A | 4/1998 | Tolkoff et al. |
| 5,769,828 A | 6/1998 | Jonkman |
| 5,776,111 A | 7/1998 | Tesio |
| 5,792,094 A | 8/1998 | Stevens et al. |
| 5,797,869 A | 8/1998 | Martin et al. |
| 5,800,384 A | 9/1998 | Russell et al. |
| 5,800,414 A | 9/1998 | Cazal et al. |
| 5,807,311 A | 9/1998 | Palestrant |
| 5,807,318 A | 9/1998 | St. Goar et al. |
| 5,810,789 A | 9/1998 | Powers et al. |
| 5,814,016 A | 9/1998 | Valley et al. |
| 5,833,671 A | 11/1998 | Macoviak et al. |
| 5,947,953 A | 9/1999 | Ash et al. |
| 5,961,486 A | 10/1999 | Twardowski et al. |
| 5,976,103 A | 11/1999 | Martin |
| 5,989,206 A | 11/1999 | Prosl et al. |
| 6,001,079 A | 12/1999 | Pourchez |
| 6,126,631 A | 10/2000 | Loggie |
| 6,156,016 A | 12/2000 | Maginot |
| 6,161,547 A | 12/2000 | Barbut |
| 6,190,349 B1 | 2/2001 | Ash et al. |
| 6,206,849 B1 | 3/2001 | Martin et al. |
| 6,217,527 B1 | 4/2001 | Selmon et al. |
| 6,280,423 B1 | 8/2001 | Davey et al. |
| 6,293,927 B1 | 9/2001 | McGuckin, Jr. |
| 6,387,087 B1 | 5/2002 | Grooters |
| 6,443,922 B1 | 9/2002 | Roberts et al. |
| 6,540,714 B1 | 4/2003 | Quinn |
| 6,620,118 B1 | 9/2003 | Prosl et al. |
| 6,638,242 B2 | 10/2003 | Wilson et al. |
| 6,682,519 B1 | 1/2004 | Schon |
| 6,695,832 B2 | 2/2004 | Schon et al. |
| 6,712,797 B1 | 3/2004 | Southern, Jr. |
| 6,723,084 B1 | 4/2004 | Maginot et al. |
| 6,786,884 B1 | 9/2004 | DeCant, Jr. et al. |
| 6,814,718 B2 | 11/2004 | McGuckin, Jr. et al. |
| 6,858,019 B2 | 2/2005 | McGuckin, Jr. et al. |
| 7,074,213 B2 | 7/2006 | McGuckin, Jr. et al. |
| 7,077,829 B2 | 7/2006 | McGuckin, Jr. et al. |
| 8,323,227 B2 | 12/2012 | Hamatake et al. |
| 2002/0087108 A1 | 7/2002 | Maginot et al. |
| 2002/0091362 A1 | 7/2002 | Maginot et al. |
| 2002/0099327 A1 | 7/2002 | Wilson et al. |
| 2002/0183781 A1 | 12/2002 | Casey et al. |
| 2002/0188167 A1 | 12/2002 | Viole et al. |
| 2003/0032918 A1 | 2/2003 | Quinn |
| 2003/0088213 A1 | 5/2003 | Schweikert et al. |
| 2003/0093027 A1 | 5/2003 | McGuckin et al. |
| 2003/0093029 A1 | 5/2003 | McGuckin et al. |
| 2003/0149395 A1 | 8/2003 | Zawacki |
| 2003/0153898 A1 | 8/2003 | Schon et al. |
| 2003/0187411 A1 | 10/2003 | Constantz |
| 2004/0054321 A1 | 3/2004 | Schon et al. |
| 2004/0059314 A1 | 3/2004 | Schon et al. |
| 2004/0065333 A1 | 4/2004 | Wilson et al. |
| 2004/0075198 A1 | 4/2004 | Schweikert et al. |
| 2004/0182102 A1 | 9/2004 | Portelli |
| 2004/0193102 A1 | 9/2004 | Haggstrom |
| 2005/0033222 A1 | 2/2005 | Haggstrom et al. |
| 2005/0131341 A1 | 6/2005 | McGuckin et al. |
| 2006/0004325 A1 | 1/2006 | Hamatake et al. |

(56) References Cited

U.S. PATENT DOCUMENTS

FOREIGN PATENT DOCUMENTS

| WO | 9106845 | A2 | 5/1991 |
|---|---|---|---|
| WO | 97/06845 | | 2/1997 |
| WO | 9717102 | | 5/1997 |
| WO | 98/17337 | | 4/1998 |
| WO | 9817337 | A1 | 4/1998 |

OTHER PUBLICATIONS

PCT/US2005/023451 filed Jun. 30, 2005 Search Report dated Oct. 2, 2006.

PCT/US2005/023451 filed Jun. 30, 2005 Written Opinion dated Oct. 2, 2006.

U.S. Appl. No. 10/884,291, filed Jul. 2, 2004 Decision on Appeal dated May 9, 2012.

U.S. Appl. No. 10/884,291, filed Jul. 2, 2004 Final Office Action dated Aug. 12, 2009.

U.S. Appl. No. 10/884,291, filed Jul. 2, 2004 Non-Final Office Action dated Feb. 27, 2007.

U.S. Appl. No. 10/884,291, filed Jul. 2, 2004 Non-Final Office Action dated Jan. 6, 2009.

U.S. Appl. No. 10/884,291, filed Jul. 2, 2004 Non-Final Office Action dated Jul. 8, 2008.

U.S. Appl. No. 10/884,291, filed Jul. 2, 2004 Notice of Allowance dated Aug. 7, 2012.

U.S. Appl. No. 10/884,291, filed Jul. 2, 2004 Advisory Action dated Oct. 27, 2009.

TIP CONFIGURATIONS FOR MULTI-LUMEN CATHETER

PRIORITY

This application is a division of U.S. patent application Ser. No. 10/884,291, filed Jul. 2, 2004, now U.S. Pat. No. 8,323,227, which is incorporated by reference in its entirety into this application.

BACKGROUND OF THE INVENTION

In various medical applications catheters with three or more lumens are needed to deliver and/or withdraw fluid from the patients' circulatory system. For example, the physician may need to divert blood from the circulatory system through a first lumen in the catheter and at the same time reintroduce the removed blood back into the circulatory system through a second lumen. A third lumen in the catheter may be used to introduce medications and/or nutrition supplements. In another example, each of the lumens within a multi-lumen catheter may be used to introduce a different drug into a patient's circulatory system. The use of separate lumens for each drug may prevent premature mixing of the medications.

One common application of a triple lumen catheter is the use of the catheter for apheresis and for delivery of medications during chemotherapy treatment of a cancer patient. Apheresis is a process that involves the removal of whole blood in a dialysis-like fashion. In this process, blood is circulated continuously from the patient to an instrument that acts as a centrifuge or filter, allowing for the separation of specific blood parts. The processed blood is re-circulated back into the patient's body. For example, apheresis may be utilized to separate out stem cells from the blood prior to chemotherapy treatments. This is generally accomplished by hormonally stimulating the production of bone marrow to produce a high number of stem cells. The stem cells are separated from the rest of the blood parts using the triple lumen apheresis catheter. Chemotherapy drugs are then administered using a third lumen in the catheter. After a given length of Chemotherapy treatment time, the stem cells are infused back into the patient's circulatory system.

To allow these blood draws and infusions, a good access to the blood stream in a large vein may be desirable. For example, the triple lumen catheter may be inserted into the patient's subclavian vein that runs behind the clavicle to establish a central line. The proximal end of the catheter may be tunneled under the skin for 2-4 inches to emerge from the chest close to the nipple. The triple lumen catheter may be used for the collection of stem cells and for support of the patient during therapy. In addition to the chemotherapy agent, antibiotics, anti-nausea medications, blood products, and fluids may also be infused through the implanted catheter.

Examples of various multi-lumen catheters are disclosed in U.S. Pat. No. 4,894,057, titled "FLOW ENHANCED MULTI-LUMEN VENOUS CATHETER DEVICE" issued to Howes, dated Jan. 16, 1990; U.S. Pat. No. 5,221,255, titled "REINFORCED MULTIPLE LUMEN CATHETER" issued to Mahurkar et al., dated Jun. 22, 1993; U.S. Pat. No. 5,378,230, titled "TRIPLE-LUMEN CRITICAL CARE CATHETER" issued to Mahurkar, dated Jan. 3, 1995; U.S. Pat. No. 5,395,316, titled "TRIPLE LUMEN CATHETER" issued to Martin, dated Mar. 7, 1995; U.S. U.S. Pat. No. 5,399,168, titled "IMPLANTABLE PLURAL FLUID CAVITY PORT" issued to Wadsworth, Jr. et al., dated Mar. 21, 1995; U.S. Pat. No. 5,451,206, titled "TRIPLE LUMEN CATHETER" issued to Young, dated Sep. 19, 1995; U.S. Pat. No. 5,486,159, titled "MULTIPLE-LUMEN CATHETER" issued to Mahurkar, dated Jan. 23, 1996; each of which is incorporated herein by reference in its entirety.

Due to design constraints, such as dimension/size limitations for insertion into a blood vessel, maintenance of structural integrity during aspiration of blood, etc., a typical multi-lumen catheter tends to possess one or more of the following undesirable properties: high recirculation of blood, low flow rate for blood circulation and medication delivery, high phlebitis, and high tendency for aspirating lumen to suck against the vessel wall. These properties limit the catheter's efficiency in blood circulation and medication delivery, which could minimize the effectiveness of the medical intervention.

Thus, an improved multi-lumen catheter with high blood circulation efficiency and high throughput for medication delivery is desirable. The improved design may incorporate one or more of the following performance characteristics: low recirculation of blood, high flow rates of blood and medications, high flow volume of blood and medications, low phlebitis, delivery of infusates in separate lumens, no dead end openings, limited sucking against vessel wall during aspiration, durable catheter structural design, capable of being produced in high volume, low production cost, capable of being placed over a guide-wire and/or a tunneler, and attractive appearance.

BRIEF SUMMARY OF THE INVENTION

Accordingly, described herein are various multi-lumen catheters each having three or more lumens where at least two of the lumens have distal openings that are staggered along the length of the catheter. The distal openings of the catheters are arranged in various configurations. These modified catheter configurations may improve fluid throughput efficiency and decrease recirculation in the catheter.

In one variation, the catheter comprises a plurality of three or more lumens where the lumen openings at the distal portion of the catheter are staggered along the length of the catheter. Preferably, the lumens are angularly spaced apart and every one of the lumen openings directs the outflow in the axial direction toward the distal end of the catheter. The lumens of the catheter may have a pie-shape cross-section with each lumen becoming narrower toward the axis of the catheter and widening toward the outer circumferential surface of the catheter. In one example, the catheter comprises three staggered lumen openings in intervals of 2.5 cm. Each of two proximal lumens open at approximately a 150 degree angle with respect to one another, while a third lumen opens distally thereof.

In another variation, the catheter comprises two or more lumens exiting at the distal end of the catheter, and at least one lumen exiting proximally along the length of the catheter. In one example, the catheter comprises three lumens, with two of the three lumens exiting distally and the third lumen exiting proximally. Preferably, the third lumen is centrally located relative to the two other lumens. The separation between the single proximal and the dual distal lumens may decrease the possibility of recirculation while maximizing flow rate. The catheter may further comprise a beveled tip for increasing the catheter's ease of insertion while keeping infusates injected through the lumens separate until entering the high blood volume regions of the body.

In yet another variation, the catheter comprises one distal lumen opening, and a plurality of proximal lumen openings. In one variation, the proximal lumens are grouped together along the length of the catheter. The proximal lumen openings may be located at approximately the same axial location along the length of the catheter. In one example, the catheter comprises a single lumen exiting at the distal end of the catheter and two other lumens terminating at the same plane along the length of the catheter proximal to the first lumen opening. In one variation, the two lumens with proximal openings are not offset angularly. In an alternative design, the two lumens may be angularly spaced when viewed from the distal end of the catheter.

These and other embodiments, features and advantages of the present invention will become more apparent to those skilled in the art when taken with reference to the following more detailed description of the invention in conjunction with the accompanying drawings that are first briefly described.

BRIEF DESCRIPTION OF THE DRAWINGS

FIG. 3B-1 shows the plain view of the catheter from FIG. 3A seen from the distal end of the catheter down the longitudinal axis of the catheter.

FIG. 3B-2 shows the cross-sectional view of the catheter from FIG. 3A at the proximal portion of the catheter.

DETAILED DESCRIPTION OF THE INVENTION

The following detailed description should be read with reference to the drawings, in which like elements in different drawings are identically numbered. The drawings, which are not necessarily to scale, depict selected preferred embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

Before describing the present invention, it is to be understood that unless otherwise indicated this invention need not be limited to applications in humans. As one of ordinary skill in the art would appreciate, variations of the invention may be applied to other mammals as well. Moreover, it should be understood that embodiments of the present invention may be applied in combination with various fluid delivery devices and/or reservoirs for intravascular fluid/medication administration.

A triple lumen catheter is used herein as an example application to illustrate the various aspects of the invention disclosed herein. Variations of the inventions may comprise three or more lumens. It must also be noted that, as used in this specification and the appended claims, the singular forms "a," "an" and "the" include plural referents unless the context clearly dictates otherwise. Thus, for example, the term "an opening" is intended to mean a single opening or a combination of openings, "a fluid" is intended to mean one or more fluids, or a mixture thereof.

Figures 1A, 1B, 1C, 1D, 1E:
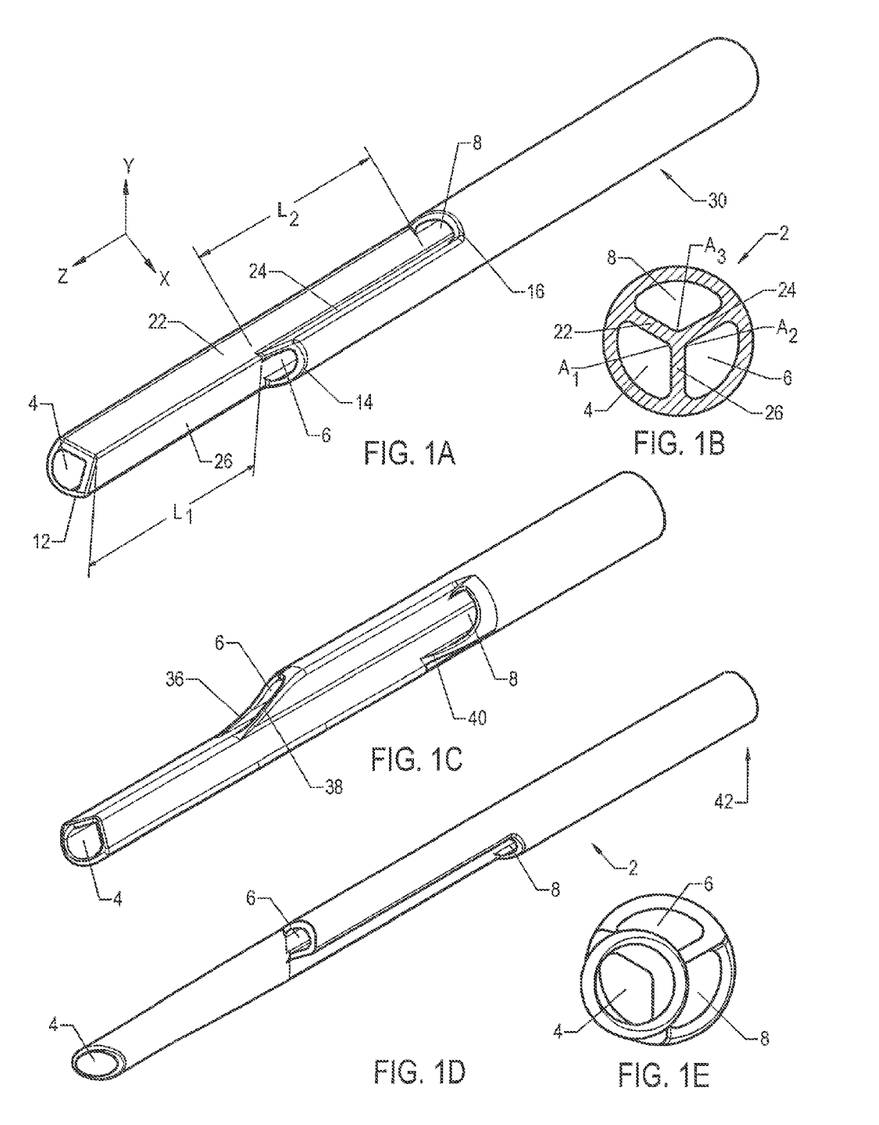
FIG. 1A shows one variation of a triple lumen catheter with staggered lumen configuration. In this variation, all three lumens are staggered along the length of the catheter with the distance between the distal lumen opening and the mid-lumen opening being marked as L1, and the distance between the mid-lumen opening and the proximal lumen opening being marked as L2.
FIG. 1B shows the cross-sectional view of the catheter from FIG. 1A sectioned at the proximal portion of the catheter. In this variation, the interior of the catheter at the proximal end is divided into three pie-shape lumens.
FIG. 1C illustrates another variation of a triple lumen catheter where the walls of the two proximal lumens extend distally to form flanges around the lumen openings thereof.
FIG. 1D illustrates another design variation with a circular distal lumen and two proximal lumens staggered at intervals along the length of the catheter.
FIG. 1E shows the plain view of the catheter from FIG. 1D, viewed from the distal end of the catheter down the tubing axis. The interior of the catheter at the distal portion comprises a circular lumen and two semi wedge/pie shape lumens.

In one aspect of the invention, the catheter comprises three or more lumens with staggered openings at the distal portion of the catheter which exit into the blood stream in intervals of predefined distance(s). Preferably, each of the lumens in the catheter has a separate opening at the distal end so that each of the lumens is in independent fluid communication with the interior of a blood vessel. FIG. 1 illustrates one variation of the catheter 2, with three lumens 4, 6, 8. The openings 12, 14, 16 for the three corresponding lumens 4, 6, 8 are staggered along the length of the catheter 2. The distance between the distal opening 12 and the middle opening 14 is indicated as "L1", and the distance between the middle opening 14 and the proximal opening 16 is indicated as "L2." L1 may be larger, smaller, or equal to L2. Preferably, the staggered distance between the openings (e.g., L1, L2) is between about 0.5 cm to about 10 cm, more preferably between about 1 cm to about 5 cm, even more preferably between about 2 cm to about 3 cm, and most preferably about 2.5 cm. For example, openings may be configured such that L1=L2=2.5 cm. In another variation, L1=1 cm, and L2=2.5 cm.

In light of the disclosure herein, one of ordinary skill in the art would appreciate that the catheter may have four, five, six, seven or more lumens, each with a corresponding opening such that the openings are staggered along the length of the catheter in various configurations that are described herein. In some variations the staggered distances between the various openings are the same, in other variations the staggered distances between lumen openings may vary. Furthermore, although in the figures shown herein, each lumen has one opening at the distal portion of the catheter, one of ordinary skill would appreciate that each lumen in the catheter may be configured with additional openings.

In the example shown in FIG. 1A, the lumens 4, 6, 8 have pie-shaped cross-sectional areas. This non-circular lumen cross-sectional design may provide improved flow rate along the length of the catheter for the three lumens. Each of the lumens 4, 6, 8 is bound by two interior walls and a portion of the outer catheter wall, and the two interior walls merge toward the central region of the catheter 2. The three interior walls may meet at the central axis of the catheter, or alternatively, they may meet off the central axis. The first 22 and the second 26 interior walls form an angle "A1", the second 26 and the third 24 interior walls form an angle "A2", and the third 24 and first 22 interior walls forms the angle "A3". In one variation, the two proximal lumens 6, 8 open at 120 degree angles with respect to each other, and the third lumen 4 forms the distal opening (i.e., A1=A2=A3=120 degree), as shown in FIG. 1A. Alternatively, the distal portion of the catheter may be configured such that A1=150 degree, A2=150 degree and A3=60 degree. In light of the disclosure herein, one of ordinary skill in the art would appreciate that the inner walls between the lumens may be configured such that the interface angles A1, A2, A3 may have various combinations. The inner walls' arrangement at the proximal portion 30 of the catheter may be configured to match the corresponding walls at the distal portion of the catheter. For example, at the proximal portion, the three interior walls 22, 24, 26 separating the three lumens may merge at the central region of the catheter 2 to form three wedge-shaped lumens 4, 6, 8, each having an angle of 120 degree (A1=A2=A3=120 degree) as shown in FIG. 1B. Alternatively, at the proximal portion of the catheter, the three interior walls 22, 24, 26 separating the three lumens may have a distinct configuration in relation to the interior walls at the distal portion of the catheter. For example, the lumens at the proximal portion of the catheter may comprise of three cylindrically shaped lumens, and transition into three pie-shaped lumens at the distal portion of the catheter.

In one variation the three lumens 4, 6, 8 have the same cross-sectional area. In another variation, the lumen 4 with the distal opening and the lumen 8 with the proximal opening have the same cross-sectional area while the lumen 6 with the middle opening has a smaller cross-sectional area in comparison to the other two lumens 4, 8. In this variation, the catheter may be implemented for dialysis, where the lumen 8 with the proximal opening may be used to aspirate blood, while the lumen 4 with the distal opening may be used to infuse the processed blood and the third lumen 6 with a smaller opening may be used to infuse medications or nutrients into the patient. In another variation, the lumen 4 with the distal opening may have a larger cross-sectional area in relation to the other two lumens 6, 8, and the two proximal lumens 4, 8 may have the same cross-sectional areas. In yet another variation, the three lumens 4, 6, 8 may have different cross-sectional areas.

The different combination of cross-sectional lumen sizes described above may be implemented in the various catheter designs described herein, and the catheters may have different cross-sectional lumen shapes. For example the lumens may have a circular or square shape instead of the pie-shapes described above. Furthermore, in light of the description herein, one of ordinary skill in the art would appreciate that any two of the three lumens on the catheter may be used for aspirating and infusing blood for dialysis or apheresis purposes, and the third lumen may be used independently for infusing fluids (e.g., saline, medications, nutrients, etc.) or extracting blood from the patient (e.g., taking blood samples). Preferably, the lumen used for aspirating blood has an opening that is proximal from the lumen used for infusing the processed/filtered blood. Also preferably, the lumens used for aspiration and infusion of blood (e.g., for filtering and/or processing) have larger lumens relative to the third lumen in order to maximize the blood processing/filtering rate. However, one of ordinary skill in the art would appreciate that this is not a necessary requirement. For some applications, it may be desirable to use a larger third lumen for delivery of medications or chemotherapy agents.

FIG. 1C illustrates another variation similar to the design shown in FIG. 1A; however, the walls of the proximal lumens 6, 8 have extended flanges 36, 38, 40 around their openings, which may direct blood flow and may provide a smoother surface profile for the catheter to minimize resistance and/or abrasion during insertion of the catheter into an orifice, such as a blood vessel. In addition, theses extended flanges 36, 38, 40 may reduce stress concentration at transitions between profiles.

Referring to FIG. 1D, yet another variation of the staggered lumen design is shown. In this variation, the catheter 2 comprises a primary lumen 4 that has a circular cross-section, while the two proximal lumens 6, 8 have non-circular cross-sections. The semi-pie-shaped lumens 6, 8, allow one to provide two additional lumens around a primary circular lumen without significantly increasing the diameter of the overall catheter. The frontal view of this catheter 2 seen from the distal end down the longitudinal axis of the catheter is shown in FIG. 1E. The proximal portion of the catheter may be configured with three pie-shaped lumens similar to the one shown in FIG. 1B.

Preferably, the two proximal lumens 6, 8 open at approximately 110 to 170 degree angles with respect to each other. More preferably, the two proximal lumens 6, 8 open at approximately 145 to 155 degree angles with respect to each other. And most preferably, the two proximal lumens 6, 8 open at approximately 150 degree angles with respect to each other. The catheter design with two proximal lumens 6, 8 having this pie-shape/semi-pie-shape design may be implemented in a catheter having a circular or semicircular distal lumen 4. In addition, the two proximal lumens 6, 8 having this pie-shape/semi-pie-shape design may be implemented in a catheter having the staggered lumen design described above, or in another design where the two proximal lumens are adjacent to one another along the length of the catheter. Such a design will be described in more detail below. The staggered design may maximize the process efficiency by decreasing recirculation of previously apheresed blood at a preferred flow rate (about 120 ml/min), while allowing the infusion of medications or TPN (Total Parenteral Nutrition) through the third lumen at a preferred flow rate (e.g., equivalent flow of a 5 Fr single lumen PICC). In addition, this design with one distal lumen formed centrally may be optimal for intravenous placement of the catheter via either a guidewire or tunneler, and may be produced in high volumes using radio frequency forming techniques.

Figures 1F, 1G:
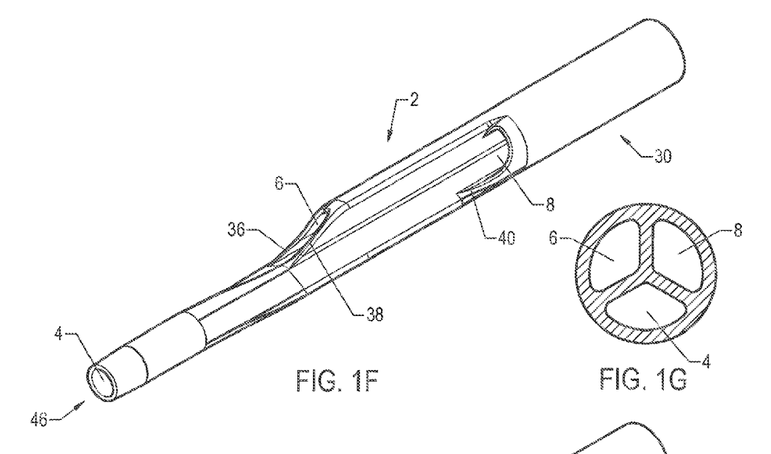
FIG. 1F illustrates another variation of the staggered lumen design with a primary circular lumen opening and two staggered proximal lumen openings. The two proximal lumens are configured with extended flanges at their distal openings.
FIG. 1G illustrates the cross-sectional view of the catheter from FIG. 1F at the proximal portion of the catheter.

FIG. 1F illustrates another design variation with a circular distal lumen opening and two proximal lumens openings 6, 8 which are staggered along the length of the catheter. The two proximal lumens 6, 8 are configured with extending flanges 36, 38, 40 at their lumen openings. As shown in FIG. 1G, in this variation the proximal portion 30 of the catheter 2 comprises three pie-shape lumens.

Preferably, the opening for each of the lumens is positioned at the distal region of the corresponding lumen, and each of the lumen openings has an outflow direction towards the distal region of the catheter along the axis of the catheter. The distal direction is shown as the Z-axis in FIG. 1A. Although lumens with openings exiting toward the distal direction of the catheter are preferred, additional side openings may also be added along the length of the catheter to increase the fluid outflow and/or intake rate. For example, side openings 52, 54 may be added to the distal portion 50 of the catheter 2 to facilitate fluid outflow from the distal lumen 4, as shown in FIG. 1H.

Figures 1H, 1I, 1J:
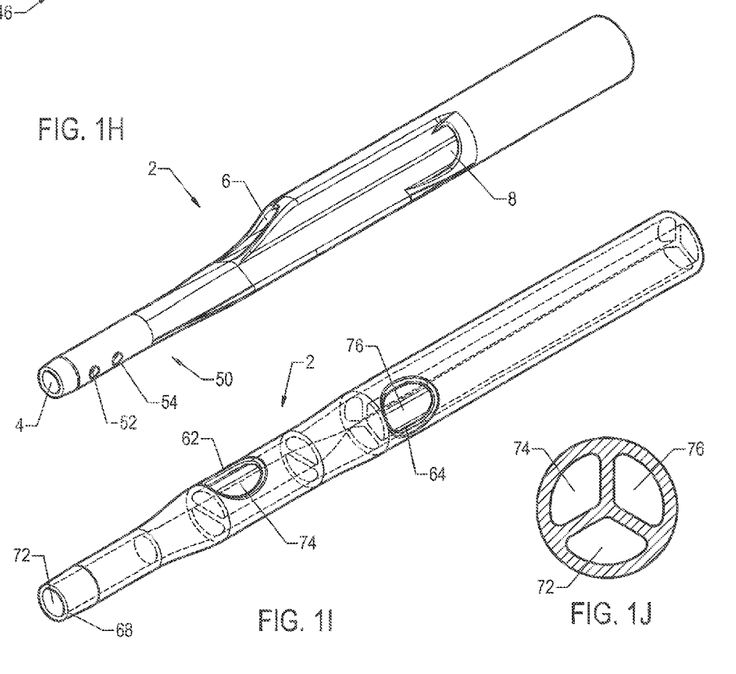
FIG. 1H illustrates yet another variation of the triple lumen staggered design with side openings on the circumferential surface for providing additional fluid exits for the distal lumen.
FIG. 1I illustrates another variation of the staggered lumen design. In this variation, the two proximal lumens are configured with openings on the circumferential surface of the catheter.
FIG. 1J shows the cross-sectional view of the catheter from FIG. 1I at the proximal portion of the catheter.

In another variation, the two proximal lumens of the catheter are configured with side openings 62, 64 that open on the circumferential surface of the catheter as the primary inflow/outflow openings, as shown in FIG. 1I. The catheter comprises three lumens. The distal lumen 72 has a circular cross-section at the distal end 68 of the catheter. The two proximal lumens are angularly positioned relative to each other, also shown in FIG. 1I. The proximal openings 62, 64 for the two proximal lumens 74, 76 are staggered along the length of the catheter and are angularly displaced from each other. The circumferential profile along the length of the catheter at the distal portion where the openings of the lumens are located is configured with a slightly tapered profile, such that the overall cross-sectional surface of the catheter decreases along the length of the catheter towards the distal end 68 of the catheter 2. In this variation, the proximal portion of the catheter comprises three pie-shaped lumens. Preferably, the three pie-shaped lumens are of equal sizes, see FIG. 1J.

In another aspect of the invention, the catheter comprises three lumens 82, 84, 86 where two 82, 84 of the three lumens 82, 84, 86 exit distally with a single centrally positioned lumen exiting proximally along the axial length of the catheter, as shown in FIGS. 2A, 2D, 2E, and 2G. The catheter may have a beveled tip to increase the catheter's ease of insertion. The two independent lumens 82, 84 at the distal end 88 allow the user to keep infusates separate until exiting the catheter into the blood stream of the patient. The proximal lumen 86 may be used for aspirating blood out of the patient's circulatory system for apheresis or dialysis applications.

The separation between the single proximal lumen 86 and dual distal lumens 82, 84 (identified as "d" in FIG. 2A) may minimize the recirculation while maximizing the flow rate. In one variation, the catheter is configured for 120 ml/min circulation rate (apheresis/dialysis flow rate) through one distal and one proximal lumen, and an equivalent flow rate of a 5 Fr PICC for the other distal lumen. Furthermore, utilizing radio frequency forming techniques, one may fabricate the catheters described above and achieve lumens with large cross-sectional areas.

Induction heating is observed when conductive materials are subjected to a radio frequency (RF) field. RF energy induces eddy currents in a tipping die made of a conductive material, and heating occurs primarily by $I^2R$ heating, that is the power dissipation in a resistive circuit. When the tipping die is also a magnetic material, additional heating effects occur from hysteresis heating, due to the friction created by the magnetic material's resistance to the rapidly changing magnetic field within the induction coil. The tipping die is placed in an induction coil forming a solenoid and the die is heated by the energy transferred from the magnetic field. The specific configuration of the solenoid may depend on the particular design requirement. By varying the current running through the solenoid, the forming temperature changes so that the thermoplastic tubing may be molded into the desired shape. One of ordinary skill in the art would appreciate that RF tipping technique such as the one described above may be implemented in the fabrication of the various catheters described herein. Furthermore, the radio frequency forming techniques may allow efficient production of catheters that are reliable and have low incidence of breakage during use. In addition, the radio frequency tipping process may allow inexpensive reproduction of catheters in large quantities in a high volume production process.

Figures 2A, 2B, 2C:
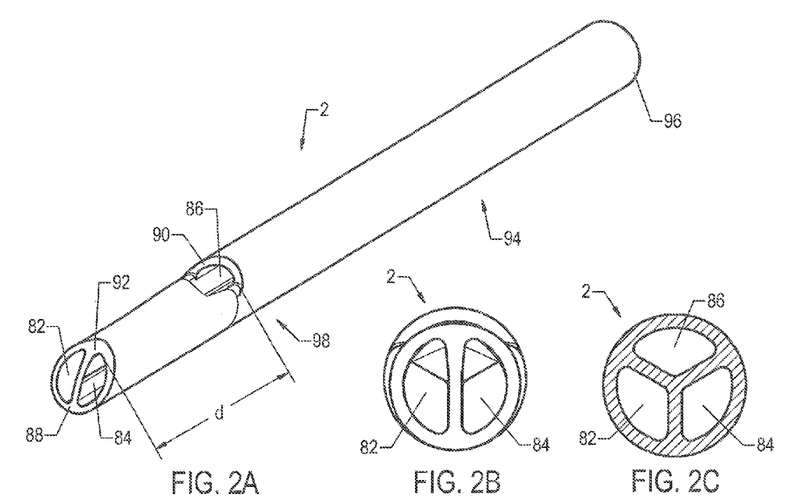
FIG. 2A illustrates another variation of a triple lumen catheter with the stagger design. In this variation, the catheter comprises two distal lumens which are positioned side-by-side and one proximal lumen. The distal lumens are designed with gradually expanding inner lumens.
FIG. 2B shows the frontal view of the catheter from FIG. 2A, as seen directly down the axis of the catheter with the two distal openings showing.
FIG. 2C shows the cross-sectional view of the catheter from FIG. 2A at the proximal portion of the catheter. As shown, the interior of the catheter at the proximal portion comprises three pie-shape lumens.
Figures 2D, 2E, 2F:
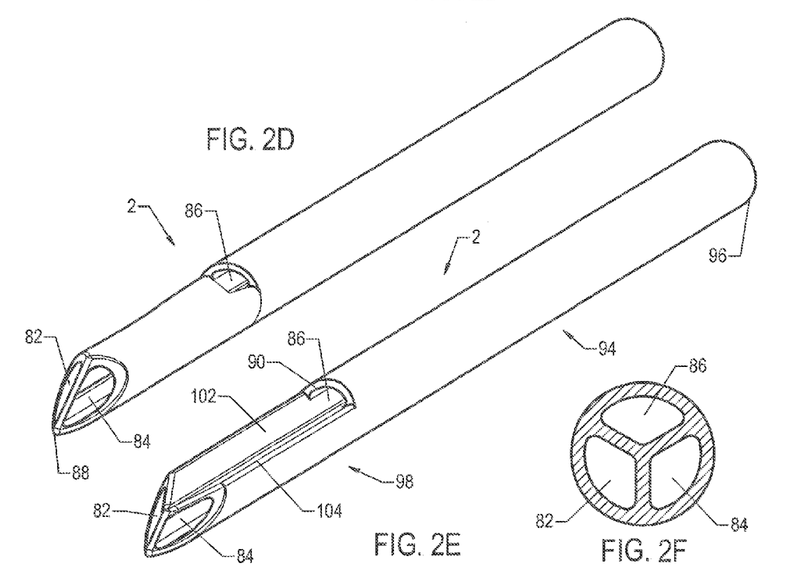
FIG. 2D shows another variation of the dual distal lumen design. The distal end of the catheter is configured with a sharper profile as compared to the catheter shown in FIG. 2A.
FIG. 2E illustrates another variation of the dual distal lumen design where the lumens of the catheter extend linearly along the length of the catheter with constant lumen cross-sectional areas along the length of the catheter.
FIG. 2F shows the cross-sectional view of the catheter from FIG. 2E at the proximal portion of the catheter.

In one variation, the two distal lumens 82, 84 are configured such that the internal lumen cross-sections increase along the length of the catheter as they approach the distal end 88 of the catheter 2. In one example shown in FIG. 2A, once the two distal lumens 82, 84 pass the proximal lumen opening 90, the diameter of the two distal lumens 82, 84 gradually increases along the length of the catheter 2 toward the distal end 88 of the catheter. This expansion in lumen diameter may allow the flow in the lumen of the catheter to have a decreased exit velocity in comparison to the fluid flow velocity along the proximal portion of the catheter where the cross-sectional area of the lumen is smaller. In the example shown in FIG. 2A, the catheter is designed to have an overall diameter that is about the same along the length of the catheter 2. The catheter's overall cross-sectional area (perpendicular to the longitudinal axis of the catheter) at the distal dual openings 92 is slightly smaller than the overall cross-sectional area at the proximal portion 94 of the catheter. FIG. 2B illustrates the frontal view (down the longitudinal axis) of the catheter as seen from the distal end 92 of the catheter 2, and FIG. 2C illustrates the cross-sectional view of the catheter at the proximal portion 94 of the catheter 2. In an alternative design, the distal portion 98 of the catheter may be configured with a larger cross-sectional area than the proximal portion 94 of the catheter. This may further decrease the exit velocity of the fluid coming out of the two distal lumens 82, 84. FIG. 2D illustrates another example of a dual distal lumen design. In this example, the distal end of the catheter 88 is configured with a sharper profile in comparison with the catheter shown in FIG. 2A.

Alternatively, the distal portion 98 of the catheter may be configured with a smaller cross-sectional area than the proximal portion 94 of the catheter. For example, the three lumens 82, 84, 86 of the catheter 2 may have constant cross-sectional areas along the length thereof, as shown in FIG. 2E. The two walls 102, 104 separating the two distal lumens 82, 84 from the proximal lumen 86 continue linearly along the length of the catheter after passing the opening 90 of the proximal lumen 86. FIG. 2F illustrates the cross-sectional view of the catheter from its proximal portion.

Figure 2G:
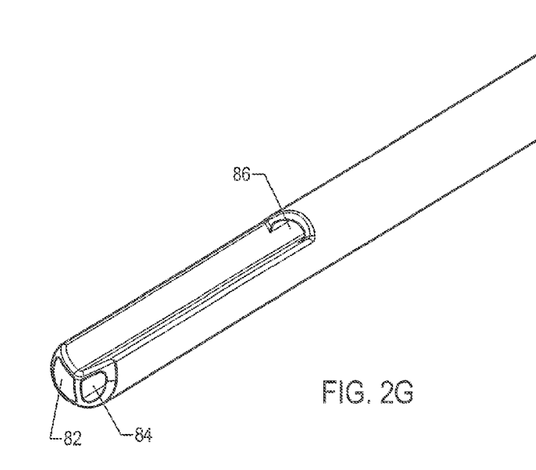
FIG. 2G illustrates another variation of the dual distal lumen design where the three lumens have varying shapes and cross-sectional areas.
Figure 2H:
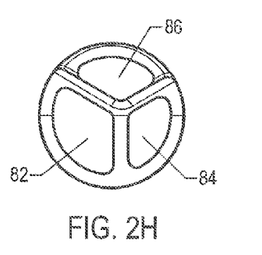
FIG. 2H illustrates a plain view of the catheter from FIG. 2G, seen from the distal end of the catheter down the axial length of the catheter. As shown, in this variation, each of the three lumens has a semi-pie-shape cross-section.

Referring to FIG. 2G, another variation is shown where the two distal lumens 82, 84 have different cross-sectional areas. In this example, the right distal lumen 82 is larger than the left distal lumen 84 at the distal portion of the catheter, as shown in FIG. 2H. One may implement this catheter for apheresis applications such that the proximal lumen 86 is used to aspirate blood, the blood is processed and infused back into the circulatory system through the right distal lumen 82, and the left distal lumen 84 is used to infuse medications and/or nutrients. Although medications may be infused through either the right 82 or left 84 distal lumen, it may be preferable to infuse the processed blood through the larger lumen 82 to increase the blood filtering/processing rate.

Figure 3A:
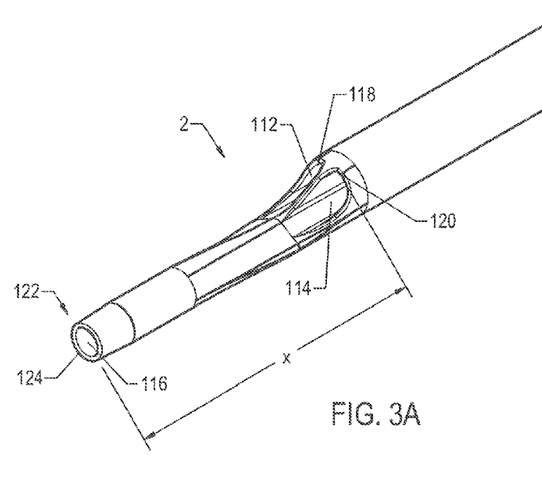
FIG. 3A illustrates another variation of the stagger lumen design where the catheter comprises two proximal lumens positioned side-by-side and a distal lumen centrally positioned relative to the two proximal lumens.

In yet another aspect of the invention, the catheter 2 is designed with two proximal lumens 112, 114 and one distal lumen 116. Examples of this design are shown in FIGS. 3A, 3C, 3D and 3F. This design may minimize recirculation due to the distance "x" (as shown in FIG. 3A) between the two proximal 112, 114 and one distal 116 lumen while simultaneously maximizing the flow rates and flow volumes. For example, the catheter may be configured for 120 ml/min circulatory flow rate at 250 mmHg through the distal and one proximal lumen, and an equivalent flow rate that is equal or better than 5 Fr PICC for the other proximal lumen. Preferably, the recirculation of the catheter is less than 5% at 120 ml/min. In addition, the single distal lumen 116 may allow easy placement of the catheter 2 using a guidewire or tunneler through the distal lumen 116. Infusate such as medications, chemotherapy agents or nutrients may be delivered independently through one of the proximal lumens while the other proximal lumen may be used for aspiration of blood or for delivery of other fluids. In addition, similar to the other catheters described above, this design may be easily produced in high volume relatively inexpensively utilizing radio frequency techniques.

Figure 3B:
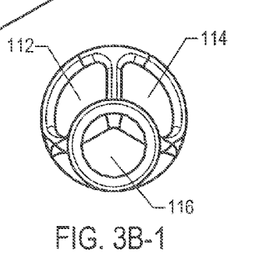
Figure 3B:
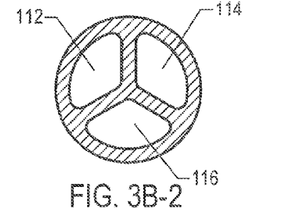

In one variation, the catheter comprises a central lumen 116 with a circular cross-sectional area at the distal end, and two proximal lumens 112, 114 with their openings 118, 120 positioned side-by-side and proximal to the distal end 124 of the catheter. The distance between the two proximal lumen openings 118, 120 and the distal lumen opening 122 is indicated as "x". Preferably, x is between about 1 cm to about 10 cm, more preferably about 2 cm to about 5 cm, even more preferably about 2 cm to about 3 cm, and most preferably about 2.5 cm. As shown in FIG. 3A, in this example, the two proximal lumens 112, 114 open at 120 degree angles with respect to each other. Alternatively, the two proximal lumens may be designed to open at other angles (e.g., 150 degrees). The cross-sectional areas of the lumen openings may be pie-shaped. In this example, all three of the lumens 112, 114, 116 direct fluid flow to exit along the axial direction of the catheter toward a distal region beyond the catheter. FIG. 3B-1 illustrates the frontal plain view of the catheter 2 seen from the distal end of the catheter down the longitudinal axis of the catheter, showing the distal opening 116 centrally positioned in relation to the two proximal lumen openings 118, 120. In this particular variation, the three lumens are designed to have three equal pie-shape lumens along the length of the catheter from the proximal end of the catheter to the proximal openings 118, 120. The cross-sectional view of the catheter at the proximal portion of the catheter is represented by FIG. 3B-2. The two proximal lumens 112, 114 terminate at 118 and 120 at the distal portion of the catheter, and the distal lumen 116 continues to extend in the distal direction. As shown in FIG. 3A, in this design the distal portion of the catheter expands radially along the length of the catheter from the proximal opening 118, 120 to the distal tip 124 of the catheter. The inner lumen cross-section along this distal region (i.e., between the proximal openings 118, 120 and the distal opening 124) transition from a pie-shape lumen to a circular lumen. In this design, the cross-sectional area of the distal circular opening 124 is larger then the cross-sectional area of the pie-shape opening of the distal lumen at the proximal region of the catheter. Alternatively, the catheter may be designed such that the distal circular opening has the same cross-sectional area as the cross-sectional pie-shape area of the lumen at the proximal portion of the catheter. Furthermore, the two proximal lumens' openings 118, 120 may be configured with the same cross-sectional area to support fluid flow at the same rate.

In an alternative design, one of the two proximal lumens is configured with a larger cross-sectional area than the other one of the proximal lumens. One may utilize the large proximal lumen in combination with the distal lumen to provide apheresis or dialysis, and utilize the smaller proximal lumen for infusion of medications and/or nutritional supplements.

Figures 3C, 3D, 3E, 3F:
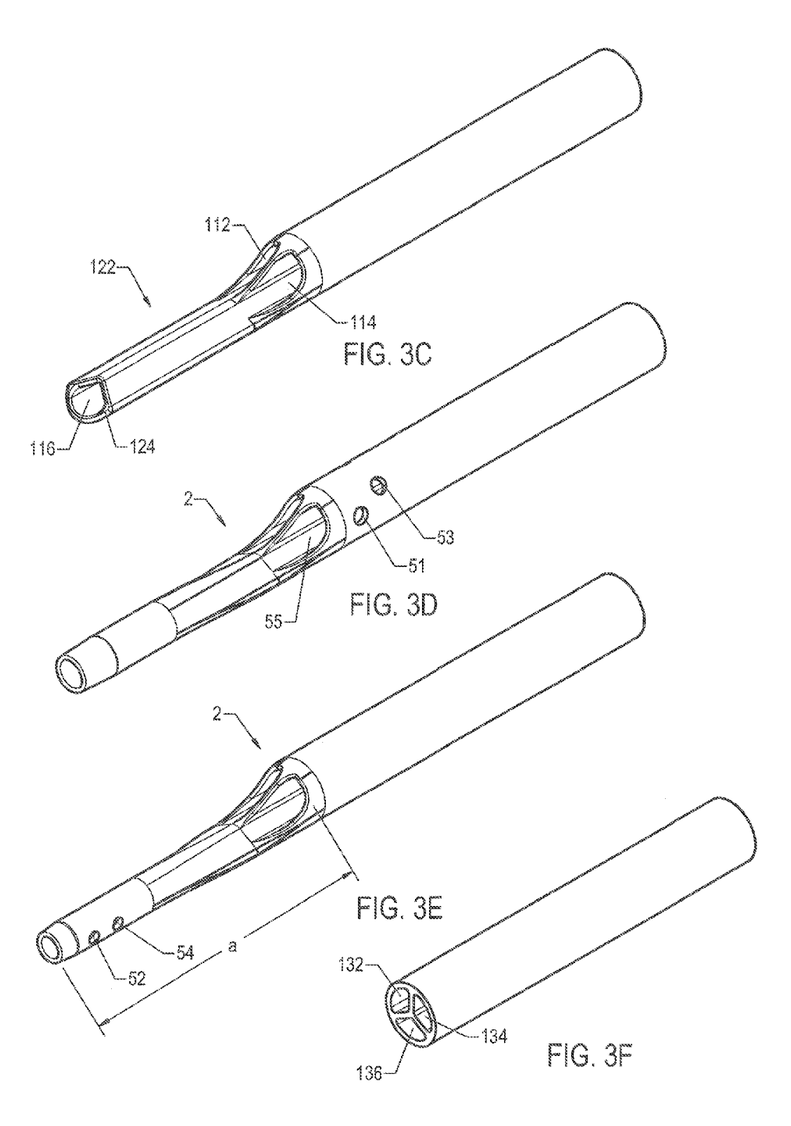
FIG. 3C illustrates another variation of the dual proximal lumen design with a non-circular distal lumen.
FIG. 3D illustrates yet another variation of the dual proximal lumen design with side openings integrated on the circumferential surface of the catheter.
FIG. 3E illustrates another variation of a dual proximal lumen design where side openings are provided for accessing the distal lumen.
FIG. 3F illustrates one variation of a proximal end configuration for a triple lumen catheter.

FIG. 3C illustrates another example of a dual proximal lumen catheter. In this example, the central lumen 116 has a non-circular cross-section. In another variation, the distal portion 122 of the catheter may be expanded such that the internal cross-sectional area of the central lumen 116 increases along the length of the catheter toward the distal end 124 of the catheter 2. For example, the catheter's tip portion 122 distal of the two proximal lumens 112, 114 may expand gradually towards the distal end 124 such that it has a funnel-shaped lumen. The increase in cross-sectional diameter of the central lumen 116 at the distal end 124 may decrease exit velocity of the fluid being infused through the central lumen 116.

The various catheter designs described herein may be further modified to reduce the risk of sucking to the blood vessel walls. This is a common design consideration in all dialysis/continuous flow catheters in order to maximize aspiration rates. In order to decrease the incidence of blockage due to sucking, side holes may be provided on the circumferential surface of the catheter. For example, side holes/openings may be provided on the distal portion of one or both of the proximal lumens that are used for aspirating blood. One variation of a catheter having side openings 51, 53 for a proximal lumen is illustrated in FIG. 3D. The side openings may allow aspiration of blood even if blockage occurs due to suction at the primary opening 55 of the lumen, and may increase flow rates and flow volumes. In another variation, side holes/openings may also be provided for the distal lumen to facilitate outflow of infused blood/fluids. Examples of catheters with side openings 52, 54 for the distal lumen are shown in FIGS. 1H and 3E. The side openings on the distal lumen may allow enhanced exit flow and provide for alternative flow paths if the end of the catheter is blocked by fibrins/clots. As one of ordinary skill in the art would appreciate, the side holes may be provided at various locations along the length of the catheter, and both the proximal and/or the distal lumens may have side holes added to facilitate aspiration and/or infusion of fluids.

In another aspect of the invention, the proximal section or the proximal end of the catheters may be molded to fit a connector of specific shape/configuration. For examples, three-lumen catheters with various distal tip designs, such as the ones shown in FIGS. 1-3, may be configured such that their proximal ends are provided with three lumens of equal proximal openings 132, 134, 136 (as shown in FIG. 3F) where each of the three proximal openings is configured to provide independent fluid communication to one of the lumens in the distal section and its corresponding distal opening. Alternatively, the lumen distribution pattern at the proximal end of the catheter may reflect the specific catheter tip design at distal end of the catheter and an adaptor may be used to connect each of the lumens to a corresponding fluid source and/or suction source. For example, the catheter may have two large pie-shape/semi-pie-shape lumens and one smaller lumen, and an adaptor with matching connectors may be used to connect the two large lumens to an apheresis or dialysis device while the third lumen is connected to a medication or chemotherapy agent infusion device (e.g., drug pump, syringe, etc.).

Figure 4A:
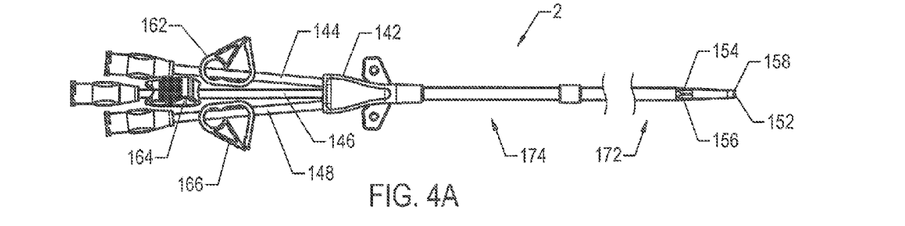
FIG. 4A illustrates a plain view of one variation of a catheter with a single distal lumen and two proximal lumen configuration where a trifurcation is connected to the proximal end of the catheter.
Figure 4B:
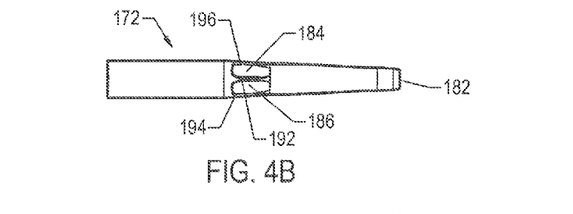
FIG. 4B illustrates the distal portion of the catheter shown in FIG. 4A.
Figure 4C:
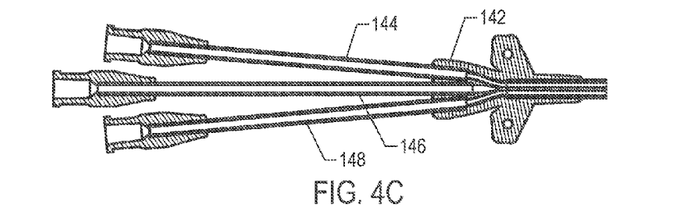
FIG. 4C illustrates the cross-sectional view of the trifurcation from the catheter system shown in FIG. 4A. The figure illustrates the independent fluid communications provided by the three separate lumens.

In one variation, the catheter 2 may be connected to a trifurcation 142 having three separate fluid lines (e.g., tubings) 144, 146, 148 for providing independent fluid infusion/aspiration for each of the corresponding lumens 152, 154, 156 in the catheter. For example, a triple lumen catheter with a distal lumen 152 and two proximal lumens 154, 156 may be adapted with a trifurcation 142 for fluid infusion and aspiration, as shown in FIG. 4A. The distal lumen 152 has an opening 182 at the distal tip 158 of the catheter. The proximal lumens each have an opening 184, 186 located proximal to the distal opening 182 along the length of the catheter, as shown in FIG. 4B. In this particular configuration, the two proximal lumens' openings 184, 186 are aligned next to each other along the length of the catheter. The left fluid line 144 is configured to provide independent fluid communication to the proximal lumen on the left 154, and the right fluid line 148 is configured to provide independent fluid communication to the proximal lumen on the right 156, and the central fluid line 146 is configured to provide independent fluid communication to the distal lumen 152, as shown in FIGS. 4A and 4C.

Optionally, tubing clamps 162, 164, 166 may be provided to seal off individual fluid lines 144, 146, 148 as desired by the operator.

Figure 4D:
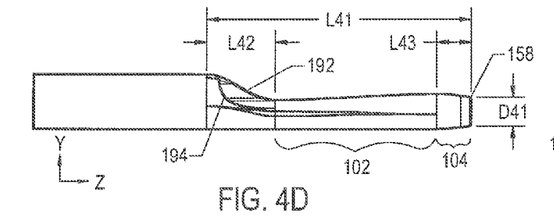
FIG. 4D is the side view of the distal portion of the catheter shown in FIG. 4A.
Figure 4E:
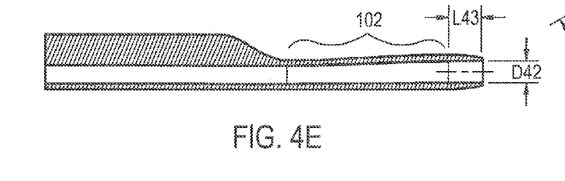
FIG. 4E is the cross-sectional view of the distal portion of the catheter shown in FIG. 4D. The cross-section is taken from the center of the catheter dividing the two proximal lumens.
Figure 4F:
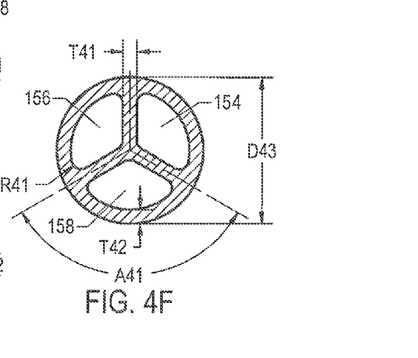
FIG. 4F is the cross-section view at the proximal portion of the catheter shown in FIG. 4A.

Furthermore, in this example the distal portion 172 of the catheter 2 is configured with a tapered profile around the two proximal lumens' distal openings 184, 186. As shown in FIG. 4D, the walls of the proximal lumens 154, 156 have fringes 192, 194, 196 extending along the length of the catheter to provide a smoother transition surface profile at the proximal lumen opening 184, 186 (L42=0.2 inches). From the proximal lumen openings 184, 186 toward the distal lumen opening 182, the catheter's height in the Y direction expands. As shown in FIG. 4E, the distal lumen's inner diameter expands along the length of the catheter at this portion 102 (i.e., between the proximal lumen opening and the distal lumen opening). At the most distal region 104 of the catheter, the outer diameter of the catheter tapers inward toward the axis of the distal lumen 152 (L43=0.1 inches). At the distal tip 158 of the catheter the outer diameter D41 of the catheter is 0.09 inches, and the inner diameter D42 of the distal lumen is 0.07 inches. FIG. 4F illustrates the cross-sectional view of the catheter 2 at the proximal portion 174 of the catheter. The outer diameter D43 of the proximal portion 174 of the catheter is 0.158 inches. The thickness T41 of the inner lumen dividing walls is 0.015 inches. The outer wall thickness T42 is 0.015 inches. The proximal portion of the catheter comprises three pie-shaped lumens 154, 156, 158 each has a 120 degree inner wall angle A41.

Figure 5A:
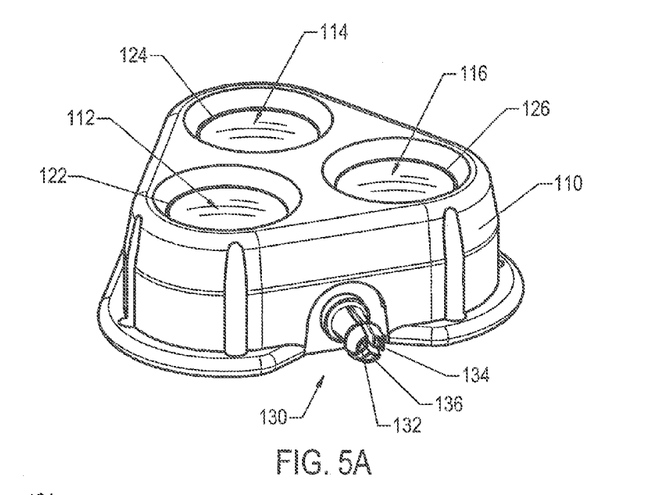
FIG. 5A shows one variation of an access port having three independent cavities each of which has an independent fluid communication path to one of the lumens at the access port connection interface.
Figure 5B:
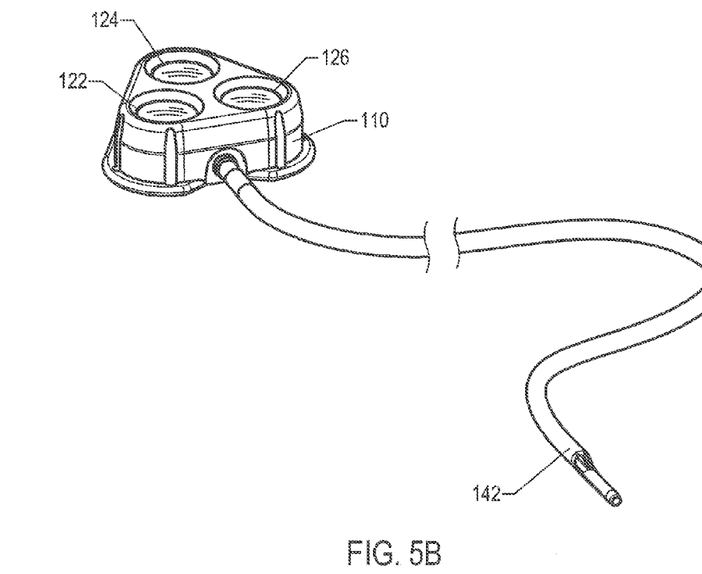
FIG. 5B illustrates an example of a triple lumen catheter with staggered lumen openings connected to an access port with three fluid cavities.

In another variation, a triple cavity port 110, such as the one shown in FIG. 5A, may be connected to the proximal end of the catheter 2 to provide the fluid infusion/aspiration interface. In this example, the access port comprises three independent fluid cavities 112, 114, 116, each of which is covered with a septum 122, 124, 126. The right cavity 112 is in independent fluid communication with the right lumen 132 of the connection interface 130. The left cavity 116 is in independent fluid communication with the left lumen 134 of the connection interface 130. The center cavity 114 is in independent fluid communication with the center lumen 136 of the connection interface. The connection interface may be configured to receive a proximal end of the catheter having three pie-shaped lumens, similar to the one shown in FIG. 3F. For example, a triple lumen catheter 142 having two proximal lumens and a distal lumen may be connected to a triple cavity port 110, as shown in FIG. 5B. An operator may insert a needle through one of the septums 122, 124, 126 to access any one of the cavities 112, 114, 116 and selectively inject or aspirate fluids through any one of the proximal and distal lumens in the catheter 142. Other multi-lumen ports, including but not limited to the ones described in U.S. Pat. No. 5,399,168, may also be implemented with the catheters described herein. In light of the disclosure herein, one of ordinary skill in the art would appreciate that other fluid input interfaces may also be adapted for use with the various catheter designs disclosed herein to provide a system for infusing and/or aspirating fluids from a patient's circulatory system.

The various multi-lumen catheters described above may comprise various elastomeric materials. For example, silicone, poly/silicone blend, Tecothane, Carbothane, Tecoflex, Chronoflex, and other biocompatible elastomeric materials may be utilized to fabricate the catheters described above. Other polymeric materials that are well known to one of ordinary skill in the art that are suitable for use in manufacturing of catheters may also be applied in the present invention. These materials may be made radiopaque through the use of known radiopacifiers such as barium sulfate. For example, the catheter body may comprise of Carbothane 80A-85A with 20% BaSO$_4$.

In light of the disclosure herein one of ordinary skill in the art would appreciate that the various multi-lumen catheter designs described may be implemented in various medical procedures where independent/separate infusion and/or aspiration of two or more fluids is desired. For example, the staggered three-lumen design may be particularly useful in apheresis, dialysis, or other medical procedures requiring placement of a central line. Moreover, the catheters described herein may be placed into a patient's body with various surgical procedures well known to one of ordinary skill in the art. One example of implementing a triple lumen catheter having staggered lumens is described below.

Before implantation of the triple lumen catheter, the physician may determine proper size of catheter to use depending on the physical size and/or weight of the patient. Non-invasive imaging techniques may also be applied to assist the physician in making such determination. In one approach, a catheter having a central distal lumen and dual proximal lumens is inserted into the right internal jugular vein. The catheter is then advanced into the patient's body along the internal jugular vein. Further advancement will place the distal section of the catheter into the superior vena cava (SVC). Ultrasound, fluoroscope, radiograph, and/or other imaging devices may be utilized to assist the physician in the placement of the catheter. A radiopaque ribbon may be provided at the distal portion of the catheter and/or along the length of the catheter to improve contrast of the catheter within the images captured by the imaging device. The position of the catheter may be adjusted within the SVC and/or right atrium depending on the physician's preference. For example, it may be desirable to position the dual proximal lumen openings next to the SVC/jugular vein junction. Alternatively the openings for the dual proximal lumen may be placed next to the SVC/Right-Atrium junction. In another variation, it may be desirable to place the distal end of the catheter into the right atrium of the heart. Once the catheter is placed in the desired position, the physician may then secure the catheter in place. Optionally, the proximal end of the catheter may be tunneled underneath the skin so that it exits the skin just beneath the right clavicle and distant from the insertion site. Once the catheter has been placed, a hemodialysis machine or an apheresis machine may be connected to the catheter to start the treatment process. For example, the proximal end of the catheter may have a trifurcation connector to facilitate the connection process. Blood may then be removed through suction delivered through the catheter to one of the proximal openings of the catheter, and processed blood may be infused back into the patient's circulatory system through a distal opening on the catheter. Chemotherapy agents, antibiotics, anti-nausea medications, blood products, fluids and other medications or nutrients may be infused through a third lumen with a proximal opening on the catheter.

This invention has been described and specific examples of the invention have been portrayed. While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well. Finally, all publications and patent applications cited in this specification are herein incorporated by reference in their entirety as if each individual publication or patent application were specifically and individually put forth herein.

What is claimed is:

1. A multi-lumen catheter, comprising:
    a first interior wall separating a first lumen from a second lumen;
    a second interior wall separating the first lumen from a third lumen;
    a third interior wall separating the second lumen from the third lumen;
    a first distal opening in fluid communication with the first lumen;
    a second distal opening in fluid communication with the second lumen; and
    a third distal opening in fluid communication with the third lumen, the third distal opening positioned axially side-by-side the second distal opening at a distal end of the catheter, the first distal opening positioned proximal of the second and third distal openings.

2. The multi-lumen catheter according to claim 1, wherein the second interior wall and the first interior wall form an angle of approximately 120 degrees.

3. The multi-lumen catheter according to claim 1, wherein a first overall cross-sectional area of the catheter proximal of the first distal opening is greater than a second overall cross-sectional area distal of the first distal opening.

4. The multi-lumen catheter according to claim 1, wherein the second and third lumens increase in cross-sectional area from the first distal opening to the distal end of the catheter.

5. The multi-lumen catheter according to claim 4, wherein a first overall cross-sectional area of the catheter proximal of the first distal opening is less than a second overall cross-sectional area distal of the first distal opening.

6. The multi-lumen catheter according to claim 1, wherein the third interior wall defines a distal-most end of the catheter, and wherein a distal end of the third interior wall forms an oblique angle with respect to a longitudinal axis of the catheter.

7. The multi-lumen catheter according to claim 6, wherein the first and second interior walls extend distal of the first opening to form an outer wall section of the catheter.

8. The multi-lumen catheter according to claim 1, wherein each of the first, second, and third lumens has a constant cross-section from a proximal end of the catheter to the distal end thereof.

9. The multi-lumen catheter according to claim 8, wherein each of the first, second, and third lumens has a similar cross-sectional shape.

10. The multi-lumen catheter according to claim 8, wherein the second lumen has a cross-sectional area greater than a cross-sectional area of the third lumen.

* * * * *